United States Patent
Brandt et al.

(10) Patent No.: US 12,161,408 B2
(45) Date of Patent: Dec. 10, 2024

(54) METHOD FOR AUTOMATIC SHAPE QUANTIFICATION OF AN OPTIC NERVE HEAD

(71) Applicant: CHARITÉ-UNIVERSITÄTSMEDIZIN BERLIN, Berlin (DE)

(72) Inventors: Alexander Brandt, Wesel (DE); Ella Maria Kadas, Berlin (DE); Sunil Kumar Yadav, Berlin (DE); Seyedamirhosein Motamedi, Berlin (DE); Friedemann Paul, Berlin (DE)

(73) Assignee: CHARITÉ-UNIVERSITÄTSMEDIZIN BERLIN, Berlin (DE)

( * ) Notice: Subject to any disclaimer, the term of this patent is extended or adjusted under 35 U.S.C. 154(b) by 664 days.

(21) Appl. No.: 17/282,386

(22) PCT Filed: Oct. 4, 2019

(86) PCT No.: PCT/EP2019/076935
§ 371 (c)(1),
(2) Date: Apr. 2, 2021

(87) PCT Pub. No.: WO2020/070294
PCT Pub. Date: Apr. 9, 2020

(65) Prior Publication Data
US 2021/0378502 A1    Dec. 9, 2021

(30) Foreign Application Priority Data
Oct. 4, 2018  (EP) ..................................... 18198717

(51) Int. Cl.
*A61B 3/00*    (2006.01)
*A61B 3/10*    (2006.01)
(Continued)

(52) U.S. Cl.
CPC .......... *A61B 3/0025* (2013.01); *A61B 3/0058* (2013.01); *A61B 3/102* (2013.01);
(Continued)

(58) Field of Classification Search
CPC ..... A61B 3/0025; A61B 3/0058; A61B 3/102; A61B 3/1225; G06T 7/155; G06T 17/20;
(Continued)

(56) References Cited

U.S. PATENT DOCUMENTS

| | | | |
|---|---|---|---|
| 2003/0019933 A1* | 1/2003 | Tsikos ...................... | G06K 7/10 235/454 |
| 2003/0052169 A1* | 3/2003 | Tsikos ..................... | G06V 20/62 235/454 |
| 2015/0157202 A1 | 6/2015 | Brandt et al. | |

FOREIGN PATENT DOCUMENTS

WO    2013148687    10/2013

OTHER PUBLICATIONS

S. Lee et al "End-to End pipeline for Fourier domain optical coherence tomography of human optic nerve head" CMBES, vol. 33,No. 1 Jun. 15, 2010. (Year: 2010).*

(Continued)

*Primary Examiner* — Mohammed A Hasan
(74) *Attorney, Agent, or Firm* — JMB Davis Ben-David (57) ABSTRACT

The invention relates to a method and a computer program for automatic shape quantification of an optic nerve head from three-dimensional image data (1) acquired with optical coherence tomography, comprising the steps of:
  a) Providing (100) three-dimensional image data (1) of the retina, the image data comprising at least a portion of the optic nerve head, wherein the image data comprises pixels with associated pixel values;
  b) In the three-dimensional image data (1) identifying (200, 300) anatomic portions of the optic nerve head, (Continued)

the anatomic portions comprising a retinal pigment epithelium (RPE) portion (3) and an inner limiting membrane (ILM) portion (2);

c) Determining an RPE polygon mesh (30) for a lower boundary of the retinal pigment epithelium portion (3), wherein the RPE polygon mesh (30) extends along the lower boundary of the retinal pigment epithelium portion (3);

d) Determining an ILM polygon mesh (20) for the inner limiting membrane portion (2), wherein the ILM polygon mesh (20) extends along the inner limiting membrane portion (2);

e) Determining a morphologic parameter (10) of the optic nerve head from the RPE polygon mesh (30) and the ILM polygon mesh (20);

f) Displaying the morphologic parameter (10) of the optic nerve head and/or a representation of at least a portion of the RPE polygon mesh (30) and/or a representation of at least a portion of the ILM polygon mesh (20).

13 Claims, 5 Drawing Sheets (51) Int. Cl.
*A61B 3/12* (2006.01)
*G06T 7/155* (2017.01)
*G06T 17/20* (2006.01)

(52) U.S. Cl.
CPC ............ *A61B 3/1225* (2013.01); *G06T 7/155* (2017.01); *G06T 17/20* (2013.01); *G06T 2207/10101* (2013.01); *G06T 2207/30041* (2013.01); *G06T 2210/41* (2013.01)

(58) Field of Classification Search
CPC . G06T 2207/10101; G06T 2207/30041; G06T 2210/41; G06T 7/12; G06T 7/62; G06T 7/0012
USPC ........................................................ 351/246
See application file for complete search history.

(56) References Cited

OTHER PUBLICATIONS

Gibson et al Optic nerve head registration via hemispherical surface and volume registration, vol. 57,No. 10,Oct. 1, 2010. (Year: 2010).*

Lee et al "End-to-End Pipeline for Fourier Domain Optical Coherence Tomography of Human Optic Nerve Head", CMBES Proc., vol. 33, No. 1, Jun. 2010.

Gibson et al "Optic nerve head registration via hemispherical surface and vol. registration", Oct. 2010IEEE transactions on biomedical engineering 57(10):2592-5 DOI:10.1109/TBME.2010.2060337.

Lee et al "Exact surface registration of retinal surfaces from 3-d optical coherence tomography images", IEEE Trans Biomed Eng Feb. 2015;62(2):609-17. doi: 10.1109/TBME.2014.2361778. Epub Oct. 8, 2014.

Abramoff et al "Automated segmentation of the cup and rim from spectral domain OCT of the optic nerve head", Investigative Ophthalmology & Visual Science Dec. 2009, vol. 50, 5778-5784. doi:https://doi.org/10.1167/iovs.09-3790.

Lee et al "Segmentation of the optic disc in 3-d OCT scans of the optic nerve head", IEEE Trans Med Imaging. Jan. 2010;29(1):159-68. doi: 10.1109/TMI.2009.2031324. Epub Sep. 15, 2009.

Kadas et al: "3D Optic Nerve Head Segmentation in Idioipathic Intracranial Hypertenseion", Springer-Verlag Berlin Heidelberg (2012), pp. 262-267.

Chen et al: "Individual A-Scan Signal Normalization Between Two Spectral Domain Optical Coherence Tomography Devices", Investigative Ophthalmology & Visual Science (2013), Accepted: Apr. 16, 2013, pp. 3463-3471.

Garvin et al: "Intraretinal Layer Segmentation of Macular Optical Coherence Tomography Images Using Optimal 3-D Graph Search", IEEE Transactions on Medical Imaging (2008), pp. 1495-1505 doi:10.1109/TMI.2008.923966.

Antony et al: "A Combined Machine-learning and Graph-based Framework for the 3-D Automated Segmentation of Retinal Structures in SD-OCT Volumes", Biomedical Optics Express, vol. 4, No. 12, published: Nov. 1, 2013, pp. 2712-2728.

Rohr et al: "Point-Based Elastic Registration of Medical Image Data Using Approximating Thin-Plate Splines", Visualization in Biomedical Computing, Springer Verlag (1996), pp. 297-306.

Reis et al: "Influence of Clinically Invisible, but Optical Coherence Tomography Detected, Optic Disc Margin Anatomy on Neuroretinal Rim Evaluation", Investigative Ophthalmology & Visual Science, Apr. 2012, vol. 53, No. 4, pp. 1852-1860.

* cited by examiner

METHOD FOR AUTOMATIC SHAPE QUANTIFICATION OF AN OPTIC NERVE HEAD

CROSS-REFERENCE TO RELATED APPLICATIONS

This is the U.S. National Stage of International Patent Application No. PCT/EP2019/076935 filed on Oct. 4, 2019, which in turn claims the benefit of European Patent Application No. 18198717.3 filed on Oct. 4, 2018.

The invention relates to a method and a computer program for automatic shape quantification of an optic nerve head from three-dimensional image data acquired from optical coherence tomography.

The optic nerve head (ONH) is affected by many neurodegenerative and autoimmune inflammatory conditions. Optical coherence tomography can acquire high-resolution, three-dimensional scans of the optic nerve head. However, the optic nerve head's complex anatomy and pathology renders image segmentation a challenging task.

This task is for example addressed in US 2015/0157202 A1. US 2015/0157202 A1 teaches a method for automated optic nerve head description based on optical coherence tomography that allows modelling of deformed optic nerve heads and that allows generating shape parameters of the optic nerve head.

Two membranes define the optic nerve head region and limit the optic nerve head towards the inner and outer eye: the inner limiting membrane (ILM) and the Bruch's membrane (BM). The ILM separates the vitreous body of the eye (also referred to as the vitreous) from retinal tissue, while the BM is the innermost layer of the choroid, i.e. is the vascular layer of the eye. The BM is a membrane between the choroidea and the retinal pigment epithelium (RPE). The BM has openings through which the optic nerve extends to form the optic nerve head.

Segmenting the ILM, the RPE and identifying the openings of the BM, provides an important starting point for calculating imaging biomarkers of the optic nerve head.

Methods known in the art are image-based evaluation and modelling methods, i.e. no mathematical description is provided for the anatomic portion of the optic nerve head that allows for modelling and predicting physical properties of the optic nerve head.

An object of the present invention is to provide a method that allows for a modelling of physical properties of the anatomic features in the optic nerve head. The object is achieved by the method having the features of claim 1.

Advantageous embodiments are described in the subclaims.

According to claim 1, a method for automatic shape quantification of an optic nerve head from three-dimensional image data acquired with optical coherence tomography comprises the steps of:
a) Providing three-dimensional image data of the retina acquired with optical coherence tomography, the image data comprising at least a portion of the optic nerve head, wherein the image data comprises pixels with associated pixel values;
b) In the three-dimensional image data identifying anatomic portions of the optic nerve head, the anatomic portions comprising a retinal pigment epithelium (RPE) portion and an inner limiting membrane (ILM) portion;
c) Determining an RPE polygon mesh for a lower boundary of the retinal pigment epithelium portion, said boundary particularly corresponding to the Bruch's membrane, wherein the RPE polygon mesh extends substantially along, particularly fits to, the lower boundary of the retinal pigment epithelium portion;
d) Determining an ILM polygon mesh for the inner limiting membrane portion, wherein the ILM polygon mesh extends substantially along, particularly fits to, the inner limiting membrane portion;
e) Determining at least one morphologic parameter of the optic nerve head from the RPE polygon mesh and the ILM polygon mesh;
f) Displaying particularly a representation of the at least one morphologic parameter of the optic nerve head and/or a representation of at least a portion of the RPE polygon mesh and/or a representation of at least a portion of the ILM polygon mesh.

Optical coherence tomography (OCT) methods particularly provide image data in form of A-scans, B-scans and C-scans, wherein the term "A-scan" refers to a one-dimensional line scan oriented essentially orthogonal to the retina, the term "B-scan" refers to a two-dimensional image data particularly reconstructed from laterally shifted A-scans, and the term "C-scan" particularly refers to three-dimensional image data reconstructed from a plurality of B-scans.

In the context of the specification the direction along the A-scan is particularly referred to as z-axis, while an x- and y-axis are oriented orthogonally to the z-axis in an Euclidian coordinate system.

The z-axis therefore particularly extends from the retinal tissue towards the vitreous, particularly along the optical axis of the eye.

An image data set that is oriented differently with respect to said coordinate system can be brought into conformity with said coordinate system as known by the person skilled in the art.

The pixels of the image data particularly represent the smallest image element in the C-scan, i.e. the pixels can be voxels.

Each pixel can be associated with a two- or three-dimensional image coordinate, such that a location of the pixel or a feature comprised by the pixel can be determined.

The image data can be represented as a two-dimensional or a three-dimensional image, wherein the image is particularly a grayscale image.

The pixel values particularly carry the optical coherence tomography signal intensity information coded particular in form of a number that is particularly represented by the pixel value.

The optic nerve head is typically surrounded by various anatomic structures, wherein said anatomic structures have often times the form of layers extending essentially in the x-y plane of the image data. These layers are intermitted by the optic nerve head.

Thus, particularly the retinal pigment epithelium layer surrounds the optic nerve. The Bruch's membrane openings are located particularly at the boundary, where the optic nerve interrupts the retinal pigment epithelium, between the retinal pigment epithelium layer and the optic nerve.

According to the invention, the retinal pigment epithelium (RPE) portion is identified in the image data, wherein the RPE portion comprises at least a portion of the retinal pigment epithelium of the eye.

It is particularly one objective of the invention to find a polygon mesh that extends along the Bruch's membrane. However, as the Bruch's membrane is typically not visible or recognizable as a separate structure in OCT images unless if there are Bruch's membrane overhangs that are particular to the optic nerve head region in the vicinity of the Bruch's membrane opening, the lower boundary of the RPE portion is identified instead. As the Bruch' membrane is adjacent to the lower boundary of the RPE portion and also comparably thin, the polygon mesh for the lower boundary of the RPE portion provides an accurate description of the Bruch's membrane location and extension.

In portions where the Bruch's membrane is visible or distinguishable, e.g. at membrane overhangs close to the optic nerve head region, the RPE polygon mesh extends along the Bruch's membrane.

The term "lower boundary" in the context of the specification refers to a limit of the RPE portion that faces away from the vitreous. The term "lower boundary" particularly refers to the surface of the RPE that faces away from the vitreous. In contrast, an upper boundary of the RPE portion refers to a surface of the RPE membrane that faces the vitreous. Therefore, two boundaries can be identified from the RPE portion in the OCT image data. As the RPE membrane is typically very thin and thus is represented only as a thin layer in the OCT data, the term "lower" and "upper" boundary particularly refer to the faces of the membrane.

Also, the inner limiting membrane (ILM) portion is identified in the image data comprising at least a portion the inner limiting membrane.

The term "identify" particularly refers to a segmentation, i.e. particularly to an extraction of pixels that have the feature in question imaged onto them.

There is a variety of methods relating to the segmentation of anatomic portions in OCT image data.

The identification of the lower boundary of the retinal pigment epithelium (RPE) portion and the inner limiting membrane (ILM) portion is particularly facilitated fully automatic, particularly by a computer program being executed on a computer.

Due to the comparably poor signal to noise ratio of optical coherence tomography images the identification of the RPE and ILM portion often times leads to noisy RPE and ILM layers.

Therefore, according to another embodiment of the invention, the RPE portion and/or the ILM portion are processed further before the RPE polygon mesh and/or the ILM polygon mesh are determined for the respective portion.

Such processing for example comprises smoothing, interpolating, and/or iterative estimation of the respective portion, the latter particularly by iteratively removing outliers in the respective portion.

Once the RPE portion and ILM portion are identified and particularly processed accordingly, a RPE polygon mesh is determined for the lower boundary of the RPE portion and an ILM polygon mesh is determined for the ILM portion, such that a good coincidence between the portion and the respective polygon mesh is achieved and the polygon meshes extend substantially along and in the respective portion.

The RPE polygon mesh and the ILM polygon mesh provide a less complex representation of the lower boundary of the RPE portion, i.e. the Bruch's membrane and the ILM portion respectively. Thus, while the RPE polygon mesh essentially fits to the lower boundary of the RPE portion (and thus the Bruch's membrane), it can deviate particularly on a scale in the order of the size of a polygon face. The same holds true for the ILM portion and the corresponding ILM polygon mesh.

The polygon mesh for the lower boundary of the RPE portion and the polygon mesh for the ILM portion allow a physical modelling of important properties of the ONH.

Polygon meshes allow for an approximation of a complex surface extending in three dimensions, wherein the approximation is particularly a simplified representation of the underlying lower boundary of the RPE portion or ILM portion. The polygon meshes allow for efficient calculations of physical properties and characteristics and for simulating or estimating physical properties of the optic nerve.

This is not possible by conventional image-based segmentation methods that solely determine a shape of the optic nerve head.

In particular, traditional morphometry methods determine shape parameters such volume, size or lengths of anatomical portions and are based on layer segmentation that result in 2.5 dimensional surfaces, i.e. a graph function on an XY-grid. In contrast, the present invention is capable to calculate morphologic parameters, such as the above named shape parameters, using three-dimensional manifold surfaces of the ILM and lower boundary of the RPE portion.

According to another embodiment the faces and/or the edges of the RPE polygon mesh and the ILM polygon mesh are assigned with physical property such as for example a spring constant or an elasticity module.

Moreover, an interaction between the RPE polygon mesh and/or the ILM polygon mesh can be established such that physical properties like pressure or deformation forces acting on the optic nerve head can be estimated.

Calculations can be performed faster and more efficient on polygon meshes for example by means for a finite element approach.

The approximation of the RPE portion and ILM portion with polygon meshes allows a more efficient calculation of the morphologic parameter while sustaining a high precision in the such determined parameter.

The morphologic parameter is particularly a shape parameter, particularly relating to a geometric and/or physical property of the optic nerve head.

In case the morphologic parameter is a shape parameter, said shape parameter for example relates to a size, a shape or another property that relates to the geometry of the optic nerve head.

The evaluation of the morphologic parameter is known to be the basis for diagnosis of several neurodegenerative diseases.

The at least one morphologic parameter particularly provides information about a geometry, a topology, a volume or a size of a region of interest of the ONH.

Outputting of the morphologic parameter or the RPE polygon mesh or the ILM polygon mesh particularly involves the displaying of particularly a graphical representation of the at least one morphologic parameter, the RPE polygon mesh and/or the ILM polygon mesh.

The displaying of the abovementioned entities is particularly facilitated by means of a display or a video projector.

The determination of the morphologic parameter from the RPE polygon mesh and the ILM polygon mesh particularly involves computer-based operations that process information (like position and orientation) of the vertices, edges and faces of the respective polygon mesh in order to arrive at the morphologic parameter. The computer-based processing particularly involves a finite element analysis of the respective polygon mesh.

According to another embodiment of the invention, the RPE polygon mesh extends over a region of the optic nerve.

According to another embodiment of the invention, the RPE polygon mesh and the ILM polygon mesh each comprise, particularly consist of, vertices, faces and particularly edges, wherein for each face of the ILM polygon mesh a corresponding vertex of the RPE polygon mesh is determined, such that a correspondence between the ILM polygon mesh and RPE polygon mesh is established, particularly wherein the polygon meshes are aligned relatively to each other based on the established correspondence.

This embodiment allows establishing a correspondence between the RPE polygon mesh and the ILM polygon mesh that allows for processing also image data stemming from the slant scans.

This embodiment allows for a precise computation for example of an ONH volume. Particularly, this embodiment allows for the use of tetrahedrons to compute such ONH volume.

Since a height of the tetrahedrons depends on corresponding points of the RPE and ILM polygon meshes, establishing this correspondence is crucial.

The RPE polygon mesh can comprise a different number of faces and vertices as the ILM polygon mesh.

According to another embodiment of the invention, the vertices of the RPE polygon mesh are arranged on a regular grid, particularly at fixed distances to each other, more particularly on a rectangular grid.

According to another embodiment of the invention, the RPE vertices extend in a single plane, particularly in a plane orthogonal to an A-scan direction or in an x-y plane of the image data.

That the RPE polygon mesh extends in a single plane can be achieved for example by a corresponding projection or transformation that is particularly applied to the ILM polygon mesh, the image data, the ILM portion, the RPE portion and/or to the Bruch's membrane and the Bruch's membrane openings.

According to another embodiment of the invention, a projected ILM polygon mesh is generated from a projection of the ILM polygon mesh on the RPE polygon mesh, particularly by a projection onto the x-y plane of the image data comprising the RPE-polygon mesh.

The faces of ILM polygon mesh corresponding to the vertices of the RPE polygon mesh, particularly the RPE polygon mesh in the x-y plane, are particularly determined using the projected ILM polygon mesh.

According to another embodiment of the invention, pixels of the three-dimensional image data having openings in the Bruch's membrane (BMO) imaged on them are automatically identified in the image data, wherein from the identified pixels comprising the Bruch membrane openings a set of points is generated representing the Bruch's membrane openings, particularly wherein the points enclose a Bruch's membrane opening region.

Particularly from each B-scan where the RPE layer is interrupted by the optic nerve head, two points representing the Bruch's membrane opening are identified.

The Bruch's membrane opening is an anatomical structure in the retina. Moreover, the openings in the Bruch's membrane can be used to determine important morphologic parameters.

Again, as the Bruch's membrane is typically invisible in OCT images unless if there are Bruch's membrane overhangs that are particular to the optic nerve head region in the vicinity of the Bruch's membrane opening, particularly the RPE portion is used for identifying the Bruch's membrane openings.

According to another embodiment of the invention, the RPE polygon mesh extends and/or is continued particularly with a plurality of faces over the Bruch's membrane opening, particularly such that the RPE polygon mesh covers the region enclosed by the set of points limiting the Bruch's membrane opening.

According to another embodiment of the invention, an oval, particularly an ellipse or a circle is fitted to the points representing the Bruch's membrane openings, wherein the oval encloses a Bruch's membrane opening region and wherein the oval is comprised by a plane particularly extending orthogonally to an A-scan direction of the image data or in an x-y plane of the image data.

The Bruch's membrane opening region, while being enclosed by the oval, particularly also extends along the A-scan direction or the z-axis of the image data, such that a volume segment is defined. The volume segment has particularly a cylindrical shape, with the oval as the base area.

While the points in the set comprising the Bruch membrane openings can have coordinates that differ along all three-dimension, and in particular also along the z-axis or A-scan direction, the fitting of an oval to the set of points yields an oval that extends in a single plane.

The position along the A-scan direction or z-axis is therefore determined by an optimization method for fitting said oval to the set of points. The optimization method can for example be based on a least-square minimization of the distance of the points to the fitted oval.

The oval allows de-noising the Bruch's membrane opening region and a simple though correct representation of the said region. The oval and particularly the associated volume segment, allows for a less complex processing of the data and calculation of the morphologic parameter, while sustaining the relevant information regarding the anatomic portions.

Moreover, according to another embodiment of the invention, an adjusted set of points representing the Bruch's membrane openings is generated, wherein the points of the adjusted set of points are located on the oval and particularly wherein neighbouring points of the adjusted set have the same distance between each other, i.e. they are arranged equidistant. This allows for a regular spacing of the points representing the Bruch's membrane opening.

According to another embodiment of the invention, the oval is transformed to a circle by an affine transformation.

The volume segment that has particularly the shape of a cylinder therefore has a circular base area after the transformation.

This embodiment allows for an even faster calculation of subsequent parameters such as the at least one morphologic parameter.

According to another embodiment of the invention, for the RPE polygon mesh a central RPE region and for the ILM polygon mesh a central ILM region is determined, wherein the respective central region is enclosed by an area corresponding to a projection of the oval onto the respective polygon mesh, particularly wherein the projection is along the A-scan direction or the z-axis of the image data.

The central ILM region and central RPE region are particularly used for the determination of the at least one morphologic parameter.

A morphologic parameter that is derived from the central regions is particularly sensitive to relevant changes of the ONH morphology, i.e. morphologic parameters derived from the respective central regions of the ILM and RPE delimited by the Bruch's membrane openings are well-suited to reflect and compare the optic nerve head morphology.

These central regions are within the particularly cylindrical volume segment. Having identified these central regions, all calculations, particularly calculations for determining the at least one morphologic parameter, can be executed on the central regions of the polygon meshes without the need of referring to the image data or further evaluating the image data.

According to another embodiment of the invention, an optic nerve head cup volume is determined, wherein the optic nerve head cup volume is calculated from the ILM polygon mesh and the RPE polygon mesh, wherein the optic nerve head cup volume is the volume enclosed by the portion of the ILM polygon mesh that extends below the particularly interpolated RPE polygon mesh.

The optic nerve head volume is particularly comprised by the central regions of the ILM polygon mesh and the central regions of the RPE polygon mesh, such that the calculations can be executed on the polygons comprised in the respective central regions, which reduces the computational load.

In the context of the specification the term "below the RPE polygon mesh" refers to a region, a point, a plurality of points and/or a volume that is located further away from the vitreous of the eye than the RPE polygon mesh, i.e. particularly closer to the lower image boundary of the B-scans of the image data.

The optic nerve head cup volume is a morphologic parameter.

According to another embodiment of the invention, an optic nerve head cup surface is calculated from the RPE polygon mesh and the ILM polygon mesh, wherein the optic nerve head cup surface corresponds to the portion of the ILM polygon mesh that extends below the RPE polygon mesh.

The optic nerve head cup surface is a morphologic parameter. The contour of the surface can provide information about ONH anomalies that can be visually inspected by medical personnel.

According to another embodiment of the invention, a bending energy is determined for the inner limiting membrane portion from the ILM polygon mesh, wherein the bending energy corresponds to a magnitude of curvature of the ILM polygon mesh, particularly wherein the bending energy is determined only for the central ILM region.

There are various means to determine a curvature of a surface and particularly for a polygon mesh. While the face of a polygon mesh does not exhibit a curvature, the overall shape of the polygon mesh can exhibit such a curvature.

A bending energy derived from the magnitude of the curvature is particularly larger for regions where the magnitude of the curvature is larger as compared to regions that exhibit a lower magnitude of curvature.

The bending energy can be determined locally for a plurality of portions of the ILM polygon mesh such that for example a color-coded ILM polygon mesh or a colour coded central region of the ILM can be displayed, wherein the colour provides information about the bending energy.

This allows for a rapid analysis and easy comprehension of the surface properties of the ILM in the central region.

The bending energy is particularly a morphologic parameter.

According to another embodiment of the invention, the RPE polygon mesh and/or the ILM polygon mesh is a triangulated surface, particularly wherein for each face of the ILM triangulated surface a corresponding vertex of the RPE triangulated surface is determined, such that a correspondence between the ILM triangulated surface and the RPE triangulated surface is established.

Triangulated surfaces are a class of polygon meshes that allow various operations performed and that are comparably easy to compute.

According to another embodiment of the invention, prior to the determination of the RPE polygon mesh for the lower boundary of the retinal pigment epithelium portion the RPE portion is smoothed particularly by means of a thin plate spline method, wherein the RPE polygon mesh is determined for the lower boundary of the smoothed retinal pigment epithelium portion.

According to another embodiment of the invention, prior to the determination of the RPE polygon mesh for the lower boundary of the retinal pigment epithelium portion the RPE portion is interpolated particularly by means of a thin plate spline method, particularly for the Bruch's membrane opening region, wherein the RPE polygon mesh is determined for the lower boundary of the interpolated retinal pigment epithelium portion.

This interpolation allows for example the precise determination of the optic nerve head cup volume and surface, as the interpolated RPE polygon mesh provides a well-defined upper boundary for the optic nerve head volume or surface.

According to another embodiment of the invention, a transformation is determined under which the retinal pigment epithelium portion becomes planar, wherein the image data and/or the ILM polygon mesh, the RPE polygon mesh and particularly the Bruch's membrane openings are transformed by the same transformation.

This process of transforming the image data as well as the associated polygon meshes is also referred to as volume flattening. Volume flattening reduces the computational complexity of subsequent processing steps.

The problem according to the invention is furthermore solved by a computer program as described herein.

The terms 'processor' or 'computer', or system thereof, are used herein as ordinary context of the art, such as a general purpose processor or a micro-processor, RISC processor, or DSP, possibly comprising additional elements such as memory or communication ports. Optionally or additionally, the terms 'processor' or 'computer' or derivatives thereof denote an apparatus that is capable of carrying out a provided or an incorporated program and/or is capable of controlling and/or accessing data storage apparatus and/or other apparatus such as input and output ports. The terms 'processor' or 'computer' denote also a plurality of processors or computers connected, and/or linked and/or otherwise communicating, possibly sharing one or more other resources such as a memory.

According to another aspect of the invention, the method according to the invention can be used as a diagnostic aid for distinguishing a healthy eye of a patient from an eye of a patient suffering from idiopathic intracranial hypertension (IIH), from autoimmune central nervous system disorders, such as multiple sclerosis (MS) and/or neuromyelitis spectrum disorder (NMOSD) and/or from a history of optic neuritis (ON), an inflammatory optic neuropathy that damages the optic nerve leading to neuroaxonal degeneration.

In the following, a description of exemplary embodiments is given by means of examples and figure description. It is shown in FIG. 1 a flow diagram depicting selected processing steps of the method according to the invention.

The invention relates to a fully automatic 3D, i.e. three-dimensional shape analysis of the optic nerve head (ONH) region. According to some embodiments it is possible to calculate novel three-dimensional shape parameters characterizing the ONH and to provide robust and reliable three-dimensional morphologic parameters that describe different aspects of the various shapes of the ONH.

In the following, the procedure to compute several three-dimensional morphologic, particularly shape parameters of the ONH including the preprocessing of the ILM surface and the RPE surface and a correspondence between them, is demonstrated.

Figure 1:
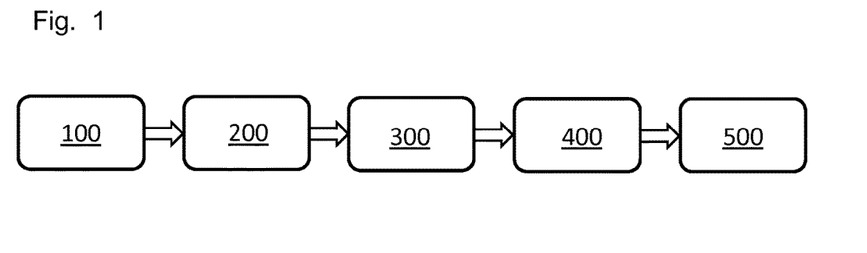

FIG. 1 shows a flow diagram, where an OCT volume scan is the input of the method, i.e. the image data provided 100 to the method comprise an OCT volume scan.

Next, the RPE surface, representing the Bruch's membrane is segmented 200 together with the Bruch's membrane opening (BMO) points. The term "RPE surface" is used interchangeably with the term "RPE polygon mesh" representing the lower boundary of the RPE portion.

It is noted that in the context of the specification the lower boundary of the RPE is identical to the Bruch's membrane layer.

In a subsequent or parallel step, the ILM surface, also referred to as the ILM polygon mesh in the context of the current specification is determined 300 from the image data.

These three anatomic portions, represented by the RPE polygon mesh, the ILM polygon mesh and the Bruch's membrane openings can be used to represent the ONH three-dimensional shape and serve as inputs for further shape analysis of the ONH.

For each face of the ILM polygon mesh, a corresponding vertex of the RPE polygon mesh is determined 400. Furthermore, a central region is determined 500 for both polygon meshes by means of a region enclosed by the BMO points, such that at least one morphologic parameter can be estimated and displayed to a user of the method.

The ILM and the RPE surfaces will be represented as $M_{ilm}$ and $M_{rpe}$, respectively and the BMO points are denoted by P. In this example, the ILM and the RPE surfaces are triangulated manifold surfaces, i.e. specific polygon meshes, and can be written in terms of a set of vertices and faces (triangles):

$$M_{ilm} = \{V_{ilm}, F_{ilm}\} \text{ and } M_{rpe} = \{V_{rpe}, F_{rpe}\}$$

The ILM and RPE surface can have different numbers of vertices and number of triangles, wherein $n_{ilm}$ and $m_{ilm}$ represent the numbers of vertices and faces in the ILM surfaces. Analogously, $n_{rpe}$ and $m_{rpe}$ denote the size of $V_{rpe}$ and $F_{rpe}$ respectively. The BMO points are represented as:

$$P = \{p_i \in R^3; i=1 \ldots n_p\}, \text{ where } n_p \text{ is the number of the BMO points.}$$

The volume scans of the ONH scans can be obtained with a spectral-domain OCT (Heidelberg Spectralis SDOCT, Heidelberg Engineering, Germany) using a custom protocol with 145 B-scans, focusing the optic nerve head with a scanning angle of 15°×15° and a resolution of 384 A-scans per B-scan. The spatial resolution in x direction is approximately 12.6 μm, in axial direction approximately 3.9 μm and the distance between two B-scans approximately 33.5 μm.

Figure 2:
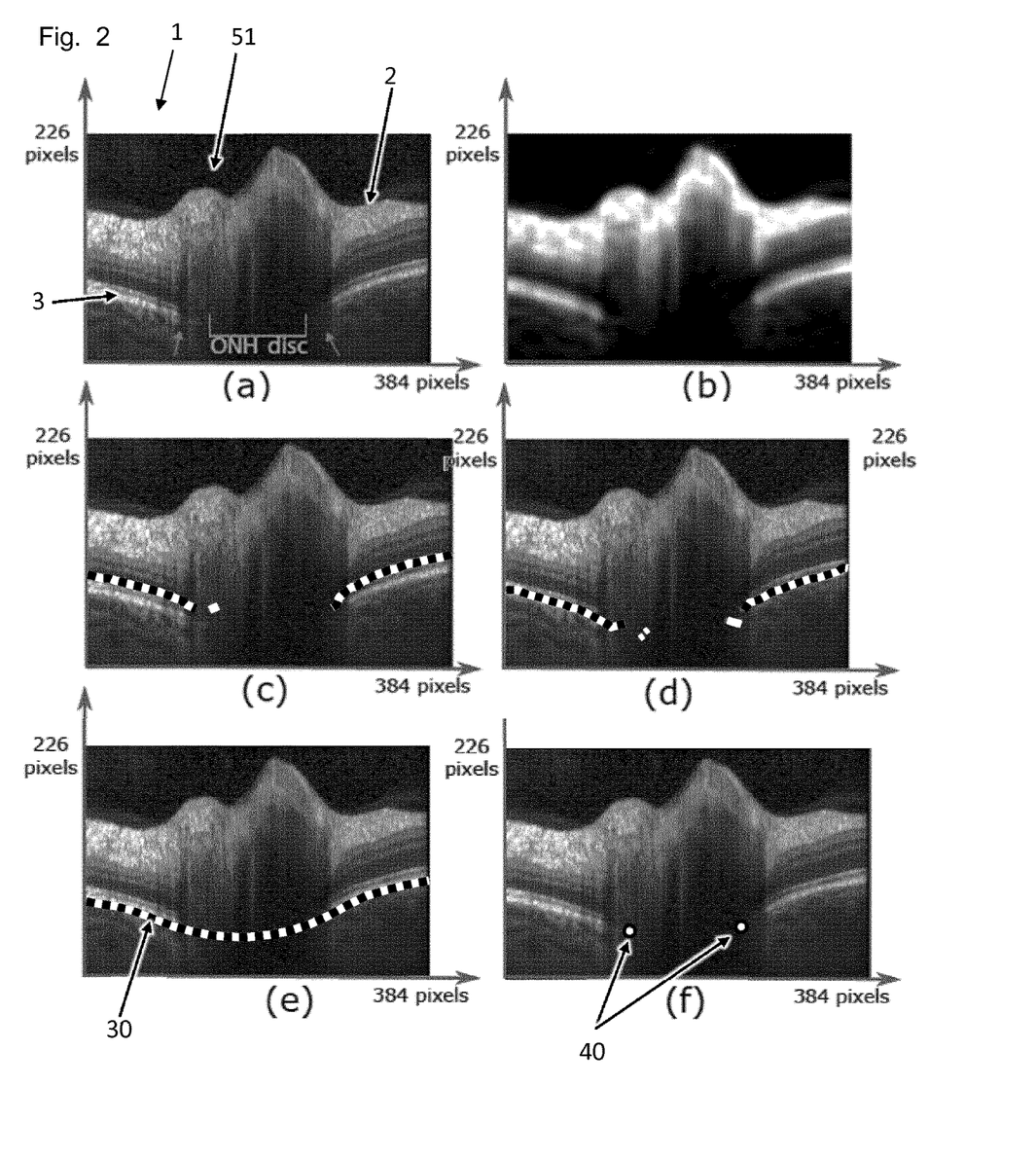
FIG. 2 a B-scan with highlighted processing steps according to the invention.

FIG. 2 shows the Bruch's membrane surface and BMO points detection exemplified using a single B-scan. FIG. 2(a) shows one B-scan of the original image data (gray arrow shows blood vessels and the shadow artifacts these produce, the delimited region is part of the ONH disc. FIG. 2 (b) shows the same B-scan after applying smoothing and intensity normalization. FIG. 2 (c) shows approximated ISOS Junction points (dotted line) after removing outliers. As a convention in the computation, the outliers detected at this step are set to have in the axial (z) direction the coordinate equal to 1. FIG. 2 (d) shows the same B-scan with an approximated upper boundary of the RPE portion, i.e. upper boundary RPE points (dotted line). FIG. 2 (e) shows the same B-scan with the smoothed and interpolated lower boundary of the RPE portion 30 (dotted line). FIG. 2(f) shows the same B-scan with the identified BMO points 40 (white dots); even in the presence of blood vessels the BMO points 40 are still detected. 384 pixels represent approximately 4402.80 μm and 226 pixels approximately 881.40 μm.

In the following a detailed example is given for generating the RPE polygon mesh 30 for the Bruch's membrane 44.

Determining the Lower Boundary of the RPE

The Bruch's membrane 44 represents the termination of the retina and is therefore an important parameter in morphometric computations. According to this example, the RPE polygon mesh 30 is determined such that it represents the Bruch's membrane. One way to segment the Bruch's membrane is taught in [1]. Several preprocessing steps are performed that are commonly employed in image data from OCT. Consider $I(q_{xy})$ the intensity of a pixel $q_{xy}$. In a first step, a Gaussian smoothing filter (σ=5 pixels isotropic with kernel size=(10 μm×14 μm) is applied on each B-scan separately. The smoothing by the Gauss filter not only reduces speckle noise present in most OCT data, but also facilitates the approximation of the two most hyperintense layers, namely the retinal nerve fiber layer (RNFL) and the RPE.

In a second step, in order to address varying intensities in the image data, a contrast rescaling on each slice (B-scan) is performed. Contrast inhomogeneities can occur in form of a B-scan having regions with different illumination or as several B-scans of the same volume with very different intensity ranges. Specifically, a histogram-based amplitude normalization method [2] is used to map the signals in the original image linearly between the pixel values [0; 1] using as low cut off the first 66$^{th}$ percentiles and as high cut off the 99$^{th}$ percentile on the histogram of the B-scan where the sampled column (A-scan) is located.

FIG. 2(b) shows a B-scan of the volume data that has been smoothed and normalized according to the above procedure. FIG. 2(a) shows the same B-scan with its original grey values.

Upper Boundary RPE Approximation

In order to approximate the upper boundary of the RPE portion 3, first the ILM portion 2 is approximated as an upper boundary for the segmenting method. At each A-scan, the first pixel from top (i.e. on the side where the vitreous 51 is located (see e.g. FIG. 2) in the smoothed and normalized volume data, $I_{SN}$ is selected, that is higher than ⅓ of the maximum value in the B-scan containing the A-scan. This provides a set of initial estimate points for the ILM, denoted by $ILM_{init}$. Next, the upper boundary of RPE is approximated. First, the image derivative, $\nabla I_{SN}$, of each B-scan (vertical gradient) using a Sobel kernel is calculated. Along each A-scan, starting from the $ILM_{init}$ set, several intermediate steps for the RPE upper boundary approximation are performed. Inner and outer segment Junction regions (ISOS) are determined by finding the first set of points p, shown in FIG. 2(c):

$$p_{xy} = \{\nabla I_{SN}(qi_{xy}) < \nabla I_{SN}(s_{xy})/3\}, s_{xy} \in ILM_{init}.$$

Starting from the set $p_{xy}$, the RPE upper boundary is approximated:

$$RPE_{upper} = \max(\nabla I_{SN}(\tilde{p}_{xy})),$$

wherein only the points below IS/OS are considered:

$$\tilde{p}_{xy} \in \{\|s_{i_{xy}} - p_{i_{xy}}\| < 60 \ \mu m\}.$$

At this stage the input is a list of points that belong to the upper boundary of RPE in each B scan. This list comprises among the points correctly positioned at the upper RPE boundary, also several outliers, especially in the presence of shadows cast by blood vessels, as well as at the region of the optic nerve head. In order to remove the outliers that lie in the upper or lower third of each B-scan, the gradient of a line consisting of upper RPE points reflecting the RPE upper boundary can be determined, and the mean value of said upper RPE points can be computed from coordinates that most likely belong to the correct upper RPE points. These coordinates represent RPE boundary points from the largest part of the gradient line between outliers (outliers in the gradient are considered to be >40 μm). The first seed point is then detected as the one closest to the mean value. Starting from this seed a $q_{seed}$, outliers are iteratively removed from $RPE_{upper}$ (points where $\|q_{seed} - q_{new}\| > 70 \ \mu m$). Similarly, outliers from the last third of the B-scan are removed. The resulting point set of one B-scan is shown by the white points in FIG. 2(d). The points removed from the $RPE_{upper}$ roughly estimate the ONH region, as well as the BMO area. Note that the ILM can have a very complex topology, while other retinal layers are missing in this area. A mask of the ONH from the removed $RPE_{upper}$ part by fitting an ellipse to its contour, $A_{ONH}$ is created.

RPE Lower Boundary Detection

The lower boundary of the RPE is denoted with $RPE_{lower}$ and is identical to the Bruch's membrane. Points with the largest negative gradient below $RPE_{upper}$, closest to the $RPE_{upper}$ are selected as the lower boundary of the RPE (i.e. if several minimum points have similar values, the point with the smallest distance to the corresponding $RPE_{upper}$ is selected). Using only the maximum gradient values leads to spurious points along each surface.

Correction of these errors is done by applying a cubic smoothing spline with a high smoothing parameter. Note that in case of presence of blood vessels, large regions of missing coordinates for the RPE might occur and the cubic spline can present deviations from the desired smooth contour.

Figure 3:
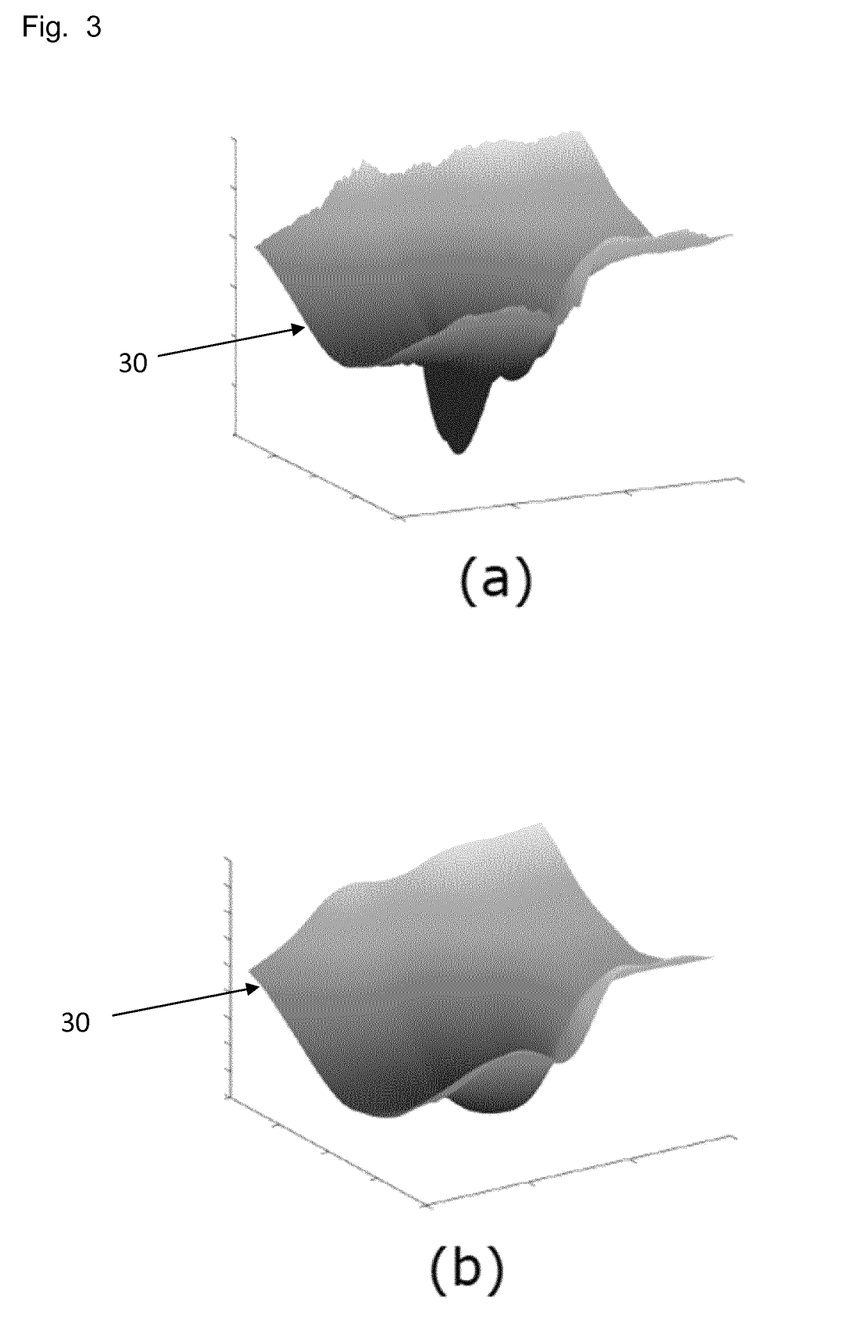
FIG. 3 a RPE surface with motion artefacts and the same RPE surface after smoothing.
Figure 4:
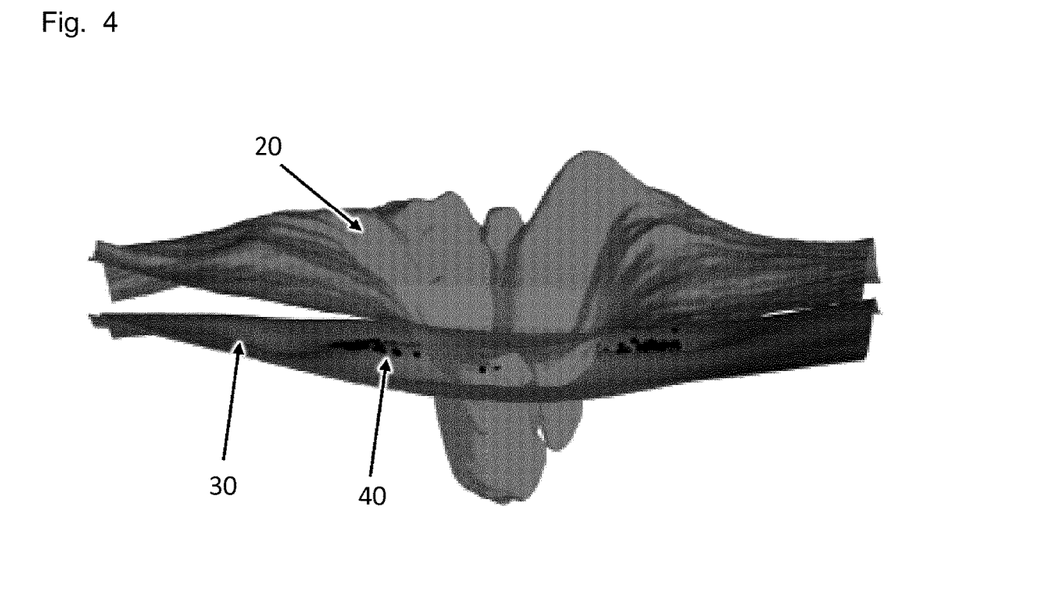
FIG. 4 representation of the RPE and ILM polygon meshes as well as the points representing the Bruch's membrane openings.

Finally, to account for motion artifacts in consecutive B-scans, but also for the natural curvature of the retina, an efficient two-stage thin-plate spline fitting (TPS) process is performed, which improves the approach proposed by [3] without making use of the orthogonal scans presented in the work of [4]. First, TPS least-square approximation is performed. The number of control points used is determined by the size of the surface along each axial dimension. At this stage, the number is set to 25% in the slow scan direction, 15%, respectively, and the control points are evenly distributed along each direction. This enables the TPS, in combination with a smoothing parameter α (c.f. [5]) set to 0.85, to create a more smoothed surface that keeps the curvature of the retina without being influenced from motion artifacts especially along the slow axis. Particularly values of α=[0.70; 0.85] provide consistent results. Extreme grid points in the original surface defined as mean+standard deviation in local non-overlapping neighborhoods of 10×10 grid points of the TPS surface are removed. Then, the actual TPS fitting similar is applied. The choice of parameters at this second step is strongly influenced by the fact that outliers at a previous stage have been removed. Specifically, for grid points 20% in the slow scan direction are used, 10% in the fast scan direction, with smoothing parameter 0.45. Consistent results were obtained for α=[0.30; 0.50]. The strategy for is to obtain a TPS closer to the data in the grid points, while smoothing the artifacts present in the position of the detected $RPE_{lower}$ points especially at the presence of blood vessels, or in the close vicinity of the approximated ONH region. Both stages are done on the $RPE_{lower}$ without including $A_{ONH}$. FIG. 3(a) shows the original RPE surface with typical artifacts in the in-between B-scans direction. These are corrected after applying our TPS approach, while keeping the shape of the original surface. The result is presented in FIG. 3(b).

The result of the RPE lower boundary 3, i.e. the Bruch's membrane, after performing the TPS is shown in FIG. 2(e).

Figure 6:
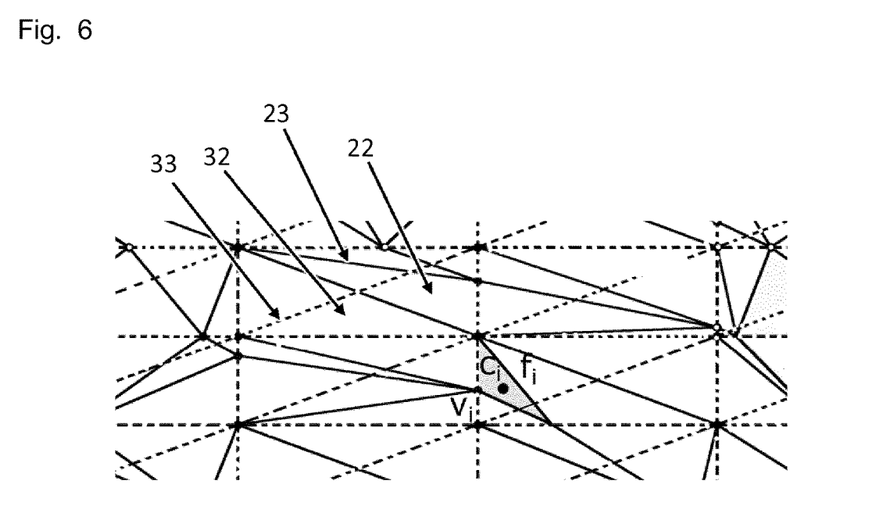
FIG. 6 RPE polygon mesh with projected ILM polygon mesh for determining the corresponding faces and vertices.

Once also the ILM surface is determined, a correspondence between the RPE polygon mesh and the ILM polygon mesh is established. For further analysis it is necessary to find the corresponding points between these two surfaces. This process is demonstrated in the following. Vertices in the RPE surface corresponding to each face ($f_i \in F_{ilm}|i=0, \ldots, m_{ilm}-1$) of the ILM surface are computed. In general, the RPE surface, represented here as a function graph: $M_{rpe}$: $R^2 \rightarrow R$, has a less complex structure compared to the ILM. In the OCT scanner, the number of the A-scans (x-direction) and the number of the B-scans (y-direction) are fixed, which creates a regular XY-grid as a domain for the RPE graph function. Therefore, the index of each vertex of the RPE surface can be computed using the numbers of x-lines (vertical lines) and y-lines (horizontal lines) and the sampling size in both directions, denoted by $\epsilon_x$ and $\epsilon_y$ respectively. The numbers of x-lines and y-lines are computed using the following equation:

$$xline = \frac{x_{max} - x_{min}}{\epsilon_x} + 1,$$

$$yline = \frac{y_{max} - y_{min}}{\epsilon_y} + 1,$$

where $x_{max}$, $x_{min}$, $y_{max}$, and $y_{min}$ are the bounding values of the RPE surface in x and y directions. For each face $f_i \in F_{ilm}$, the vertex of the RPE surface onto the XY-plane is computed, which approximates the position of the corresponding A-scan and B-scan in the volume scan. Let us consider that $c_i$ represents the centroid of the face $f_i$. To compute the corresponding vertex in the RPE surface, the face $f_i$ is projected onto the corresponding XY-plane, $\tilde{c}_i$ represents the projected centroid. The terms $\tilde{c}_{xi}$ and $\tilde{c}_{yi}$ are the corresponding x and y coordinates. The x-index ($i_x$), the y-index ($i_y$), and the vertex (i) index are computed using xline and yline in the RPE surface for the face $f_i$ using the following equation:

$$i_x = \left\lceil \frac{\tilde{c}_{x_i} - x_{min} + \epsilon_x/2}{\epsilon_x} \right\rceil,$$

$$i_y = \left\lceil \frac{\tilde{c}_y - y_{min} + \epsilon_y/2}{\epsilon_y} \right\rceil,$$

$$i = i_x + i_y \cdot xline,$$

where $\lceil \ldots \rceil$ represents the ceil function and i denotes the corresponding vertex in the RPE surface. For an accurate computation, the neighborhood of vertex i of the RPE surface is checked and the corresponding vertex is computed as:

$$\tilde{v}_i = \tilde{v}_j \in \Omega_i | \min |\tilde{c}_i - \tilde{v}_j|,$$

where $\Omega_i$ represents the 3×3 neighborhood (at XY-plane) of vertex i. The term $\tilde{v}_i$ corresponds to the projection of vertex $v_i \in V_{rpe}$ onto XY-plane. Finally, we get the set $$C = \{v_i \in \mathbb{R}^3 | i = 0, \ldots, m_{ilm} - 1\}$$

which represents the set of RPE surface vertices corresponding to each face in $F_{ilm}$. A visual representation of the correspondence computation is shown in FIG. 6, where the RPE's regular XY-grid is shown in blue and the projected ILM's vertices and edges are painted in red.

BMO Points Computation

BMO is the termination of the Bruch's membrane (BM) layer, i.e. the lower boundary of the RPE, and serves as a stable zero reference plane for ONH quantification. Thus, the BMO is an important parameter in the detection of ONH morphologic parameters. A challenge in BMO detection is the correct identification of these points 40, especially in the presence of shadows caused by blood vessels, or the border tissue of Elsching 50—a structure similar to the BM. The BMO points 40 are segmented in the three-dimensional image data directly without the use of a two-dimensional projection image in the XY-plane, as know from the state of the art.

For BMO determination the image data are flattened. This step refers to the translation of all A-scans such that a chosen boundary in the volume is flat. In this example, the retina is aligned to the smoothed $RPE_{lower}$. The alignment facilitates the volume reduction process, as well as the differentiation of BMO from other tissue.

The end-points of the rough ONH area, $A_{ONH}$ provide the starting points for BMO points detection. On each B-scan, the starting points are updated with new BMO points candidates if they meet the following conditions: 1) have minimum value in the 2D Morlet filtered image, 2) $d(p_{new}, p_{BMO-seed}) < 30$ μm, and 3) the curvature in a neighboring region of 5 voxels is almost zero to avoid including the tissue of Elsching. In case the BMO points detected in the left and right part of one B-scan overlap, the BMO starting or end region previously defined by $A_{ONH}$ are updated accordingly. An example of a pair (left and right) detected BMO points is shown in FIG. 2(f).

Figure 5:
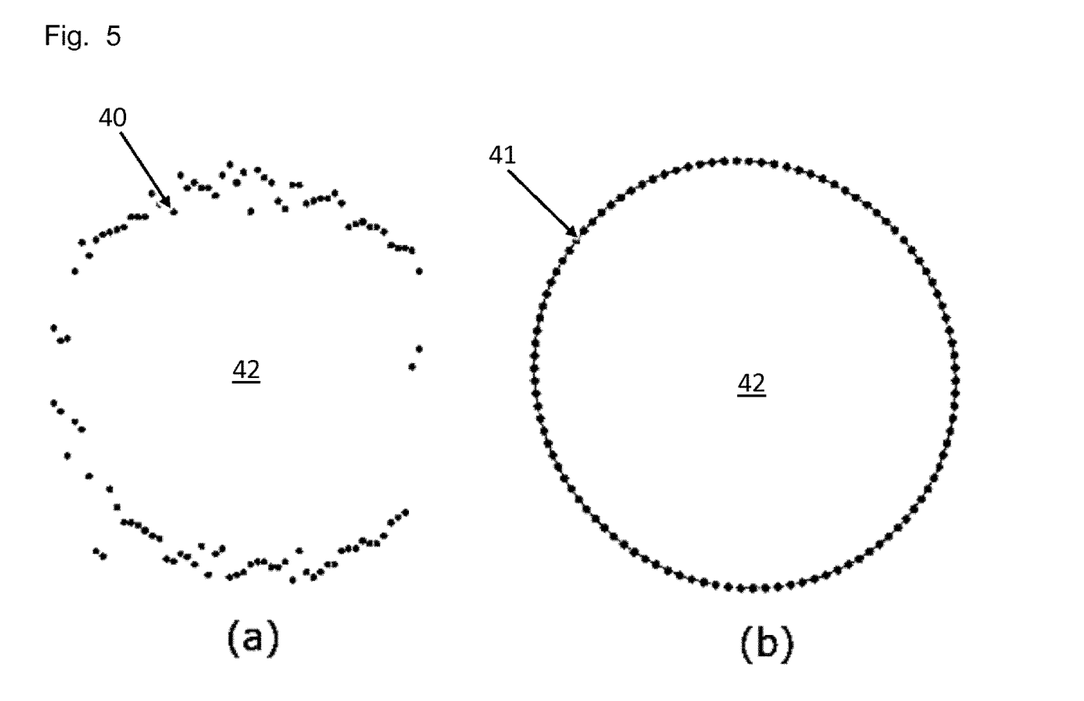
FIG. 5 Set of points representing the Bruch's membrane openings and the fitted ellipse enclosing the Bruch's membrane opening region.

Due to blood vessels around the ONH, noise components and three-dimensional OCT scan patterns, the BMO points are non-uniform and noisy as shown in FIG. 5(a). To remove these artifacts, an ellipse is fitted to the BMO points. Another key parameter in the ONH shape analysis is the center of the BMO points. This is computed as the barycenter of the all BMO points. FIG. 5 shows that the ellipse fitting is not only removing the noise but also increases the data points uniformly.

For the ONH shape analysis, the region inside the BMO points is of special interest since BMO points represent the optic disc margin. To segment this region, the elliptic representation of the BMO points in $R^2$, i.e. the fitted ellipse, along with the barycenter of the BMO points are used. First, the centers of the ILM and the RPE surfaces corresponding to the center $\tilde{p}_c$ of the BMO points are computed.

Let us consider that $\tilde{V}_{ilm}$ and $\tilde{V}_{rpe}$ represent projected sets of vertices onto XY-plane. Then, the indices of the centers of both surfaces can be computed as:

$$ilmc = j \in 0, \ldots, n_{ilm} - 1 | \min |\tilde{v}_j^{ilm} - \tilde{p}_c|$$

$$rpec = j \in 0, \ldots, n_{rpe} - 1 | \min |\tilde{v}_j^{rpe} - \tilde{p}_c|$$

where $\tilde{v}_j^{ilm} \in \tilde{V}_{ilm}$ and $\tilde{v}_j^{rpe} \in \tilde{V}_{rpe}$. The vertices $v_{ilmc} \in V_{ilm}$ and $v_{rpec} \in V_{rpe}$ represent the center of the ILM and the RPE surfaces, respectively.

To compute the BMO regions in the ILM and the RPE surfaces, the ellipse is transformed into a circle using the affine transform. Let us consider $\tilde{p}_i^e$ represents the fitted ellipse point to $\tilde{p}_i$ and $\tilde{p}_i^c$ denotes the corresponding affine transformed point on a circle of radius r. This transformation reduces the complexity of the BMO region computation and increases the speed of the method, particularly when implemented as a computer program. Now, by using the circular representation of the BMO points, the BMO regions in both RPE and ILM surfaces is computed as:

$$\Omega_{ilm} = \{f_j \in F_{ilm} | |\tilde{c}_j^{ilm} - \tilde{v}_{ilmc}| \leq r\},$$

$$\Omega_{rpe} = \{f_j \in F_{rpe} | |\tilde{c}_j^{rpe} - \tilde{v}_{rpec}| \leq r\},$$

where r is the radius of the transformed circle and $\tilde{c}_j^{ilm}$, $\tilde{c}_j^{rpe}$ represent the centroid of a face in the ILM and the RPE surfaces, respectively. The computation of the respective regions is done using the disk growing method.

With these processing steps of the image data, the central region of the ILM polygon mesh, the central region of the RPE polygon mesh as well as the BMO opening region are determined.

Determination of Morphologic Parameters 10

ONH Cup Volume 7

Figure 7:
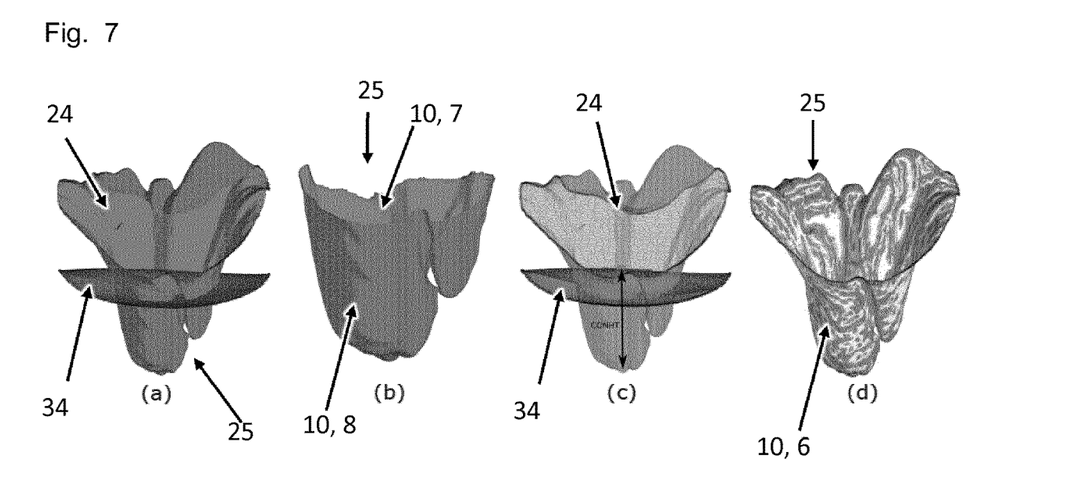
FIG. 7 a visual representation of different morphologic parameters.

The ONH cup is defined as a segment of the ILM surface 20, i.e. the ILM polygon mesh 20, particularly the central ILM region 25, which extends below the RPE surface 30 as shown in FIGS. 7(a) and (b). Note that the cup is not present in every ONH volume scan. For example, in the case of a swollen ONH, the ILM surface is always above the RPE surface. To detect the presence of the ONH cup, for each face $f_i \in F_{ilm}$ and compute its centroid $c_i$. As mentioned above, each face $f_i$ of the ILM has the corresponding vertex $v_i \in C$ in RPE. If $c_i^z - v_i^z \geq 0$ for all faces in ILM, then, there is no cup available in the ONH region. Otherwise, there is a cup. The terms $c_i^z$ and $v_i^z$ show the corresponding z-coordinates (height). Similarly, it is possible to compute the cup region:

$$\Omega_{cup} = \{f_i \in f_{ilm} | (c_i^z - v_i^z) \leq 0\},$$

where $\Omega_{cup}$ consists of faces (triangles) of ILM, which are below the RPE surface. As it can be seen from FIG. 7(b), the cup region is also a manifold surface with proper face normal orientation. To compute the volume of the cup accurately, the face normal information at each triangle of the region can be used.

The cup volume is computed using the following formula:

$$V_{cup} = \sum_{(f_i \in \Omega_{cup})} A_i h_i,$$

where $A_i$ represents the area of a triangle, which is a projection of the face $f_i$ of the ILM surface onto the XY-plane and $h_i$ is the height with respect to the RPE surface. These variables are defined as:

$$A_i = \tfrac{1}{2}(\vec{e}_0 \times \vec{e}_1), h_i = (c_i^z - v_i^z),$$

where $\vec{e}_0$ and $\vec{e}_1$ are the connected edges of the projected triangle. The cross product between the two edges will take care of the orientation of the corresponding face and enables a precise volume computation even in complex topological regions.

Central ONH Thickness (CONHT):

The CONHT is defined as the height difference between the center of the ILM and the RPE surfaces as shown in FIG. 7(c).

BMO Region Volume:

The BMO region volume is computed using the segmented ILM and RPE surfaces. For this reason the cup volume is separated from the BMO region volume such that it does not include the cup volume, if it exists. Then, the BMO region volume can be computed as:

$$\Omega_{bmo} = \Omega_{ilm} \setminus \Omega_{cup}.$$

Similar to the ONH cup volume, the BMO region volume is determined using the similar formula:

$$V_{bmo} = \sum_{(f_i \in \Omega_{bmo})} A_i h_i,$$

where $A_i$ is area of the face $f$, which belongs to the set $\Omega_{bmo}$.

Similarly, $h_i$ is also computed using the corresponding vertices in the RPE surface.

Figure 9:
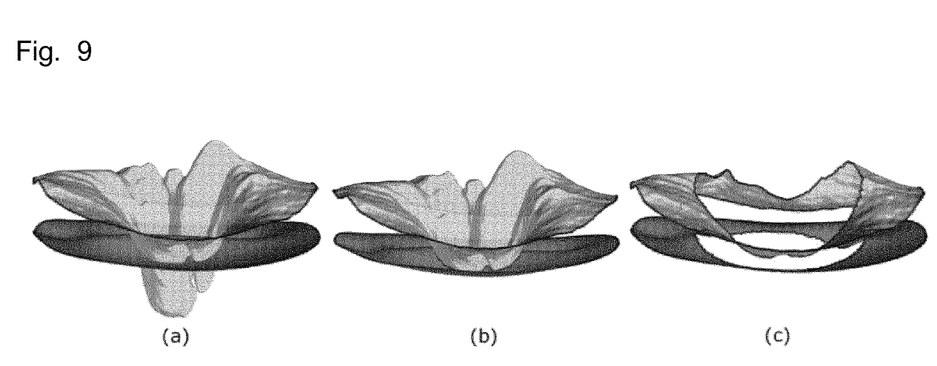
FIG. 9 a representation of various morphological parameters.

ONH Total Volume:

Similar to the ONH cup and the BMO region volumes, the ONH total volume is also computed using ILM and RPE surfaces. The total volume is computed from the circular region, with radius 1.5 mm, centered at $v_{ilmc}$ and $v_{rpec}$ for ILM and RPE surfaces respectively, as shown in FIG. 9(a). The circular regions for ILM and RPE surfaces are computed using the following equation:

$$\Omega_{1.5mm}^{ilm} = \{f_j \in F_{ilm} \| \tilde{c}_j^{ilm} - \tilde{v}_{ilmc} \| \le 1.5 \text{ mm}\},$$

$$\Omega_{1.5mm}^{rpe} = \{f_j \in F_{rpe} \| \tilde{c}_j^{rpe} - \tilde{v}_{rpec} \| \le 1.5 \text{ mm}\},$$

where $\Omega_{1.5mm}^{ilm}$ and $\Omega_{1.5mm}^{rpe}$ are the sets consisting of all faces within the 1.5 mm region of the ILM and RPE surfaces from their centers. Then, the total volume region $\Omega_{tv}$ is calculated using:

$$\Omega_{tv} = \Omega_{1.5mm} \setminus \Omega_{cup}$$

where represents $\Omega_{tv}$ the total volume region on the ILM surface as shown in FIG. 9(b), which is further employed for the total volume computation:

$$V_{tv} = \sum_{(f_i \in \Omega_{tv})} A_i h_i,$$

where $A_i$ is the area of the face $f_i \in \Omega_{tv}$ and $h_i$ is the height w.r.t. corresponding vertex in the RPE surface.

ONH Annular Region Volume:

The ONH annular region represents the ONH outer region, see FIG. 9(c). On ILM surface this region is computed using the following equation:

$$\Omega_{ab} = \Omega_{1.5\ mm} \setminus \Omega_{bmo}$$

where $\Omega_{av}$ consists of all the ILM surface faces which belong to the annular region of the ONH. The volume of the annular region is computed using the ILM and RPE surfaces correspondence.

$$V_{av} = \sum_{(f_i \in \Omega_{av})} A_i h_i.$$

The annular region volume helps to see the change in the outer region of the ONH volume in different cohorts.

Bending Energy 6:

The roughness on the ILM surface within the BMO region is an important parameter and commonly known as the bending energy on a manifold surface. The bending energy measures the fairness of a surface in terms of the curvature. In general, the outer region of the ILM surface is quite smooth and flat unlike the one inside the BMO, which has very complex topological structure. In this paper, we define the bending energy within the BMO region using the element-based normal voting tensor (ENVT). The ENVT exploits the orientation information (face normals) to compute a shape analysis operator at each face $f_i \in \Omega_{bmo}$ and is defined as:

$$M_i = \frac{1}{\sum_{f_j \in \Omega_{bmo}} a_j} \sum_{f_j \in \Omega_{bmo}} a_j n_j \cdot n_j^T,$$

where $n_j$ represents the normal of face $f_j$ and $n_j^T$ the transpose of $n_j$. The term $a_j$ is the area of the face $f_j$. To assure robustness against irregular sampling of the ILM surface, the above equation is weighted by the corresponding face area $a_j$. The ENVT, $M_i$ is a symmetric and positive semi-definite matrix, so, it can be decomposed into its spectral components:

$$M_i = \sum_{k=0}^{2} \lambda_k^i e_k e_k^T,$$

where $\lambda_k^i = \{\lambda_0^i, \lambda_1^i, \lambda_2^i\}$ are the eigenvalues of the eigenvectors and these eigenvalues are sorted in decreasing order ($\lambda_0^i > \lambda_1^i > \lambda_2^i \ge 0$). The corresponding eigenvector is denoted by $e_k$. In general, the dominant eigenvalue $\lambda_0^i$ has the corresponding eigenvector in the direction of the face normal and the remaining two eigenvectors will be aligned to the principle curvature direction on the ILM surface. On the planar region, only $\lambda_0^i$ will be significant, on the edge region, $\lambda_0^i$ and $\lambda_1^i$ will be significant and at the corners, all of these eigenvalues are significant. Using the anisotropic properties of these eigenvalues, we define the bending energy inside the BMO region using the following Equation:

$$E_b = \sum_{f_i \in \Omega_{bmo}} \lambda_2^i + \lambda_3^i,$$

where $\lambda_1^i$ and $\lambda_2^i$ are the two least dominant eigenvalues of the ENVT of the face $f_i$. FIG. 7(*d*) shows how each face of the BMO region is colored based on the bending energy. The color is scaled from white (flat regions) to dark (sharp features).

BMO-MRW:

BMO-MRW, has been proposed by [6] as a valid alternative structural measure. It computes the minimum distance between the BMO points and the ILM surface. The average BMO-MRW, denoted by $\text{avg}_{ni}$, is calculated as:

$$avg_{mrw} = \frac{1}{n_p} \sum_{i=1}^{n_p} |p_i^{mrw} - p_i^e|.$$

BMO-MRW surface area:

BMO-MRW surface area, BMO-MRA, is computed by taking the whole region defined by all BMO-MRW. The ellipse fitted BMO points $P_{2D}$ and the z-coordinates from P are combined and are represented as: $P_e = \{p_i^e \in R^3 | i=0, \ldots, n_p-1\}$.

For each point $p_i^e \in P$, a point $p_i^{mrw}$ on the ILM surface is computed:

$$p_i^{mrw} = v_j \in V_{ilm} |\min|v_j - p_i^e|.$$

The MRW points $P_{mrw} = \{p_i \in R^3 | i=0, \ldots, n_p-1\}$ are lying on the ILM surface. A A quad surface is created using point sets $P_e$ and $P_{mrw}$ by introducing edges between the corresponding vertices in both point sets and connecting the neighbor points. The number of quad elements in the MRD surface is equal to the number of points in each point sets and is represented as: $Q = \{q_i | i=0, \ldots, n_p-1\}$. MRW-MRA is computed as:

$$A_{mrw} = \sum_{q_i \in Q} a_{q_i},$$

where $a_{q_i}$ represents the area of the quad $q_i$.

BMO Area:

As shown in FIG. 5, BMO area (BMOA) represents the area under the fitted ellipse to the BMO points and is computed using the conic representation:

$$A_{bmo} = \pi r_1 r_2$$

where $r_1$ and $r_2$ are the major and minor axes of the fitted ellipse.

Experiment and Results

In order to evaluate the method according to the invention repeated-measurement reliability tests were performed, the ONH shape in healthy subjects was investigated, and tested in order determine if the method is able to detect differences in patients with diseases known to affect the ONH in form of swelling and atrophy.

In order to estimate the repeated-measurement reliability three repeated scans of each eye from ten healthy subjects were taken. These subjects were measured each in a time frame of a week, and then again in the following week. Table 1 shows the repeatability results. The method according to the invention scores highly at every parameter presented, with lowest intraclass correlation coefficient (ICC) of 0.905 for CONHT, and highest 0.998 for $V_{cup}$. The ICC and confidence intervals were estimated using the variance components from a one-way ANOVA.

The method according to the invention, was also tested with several other scan protocols of the same device (ONH cube with 73 B-scans, scanning angle of 15°×15° and resolution 384 A-scans per B-scan, spatial resolution in x direction is ≈12.6 μm, in axial direction≈3.9 μm and the distance between two B-scans≈61 μm, ONH star scan with 24 B-scans, scanning angle of 15°×15° and a resolution of 768 A-scans per B-scan, spatial resolution in x direction is ≈5.36 μm, in axial direction≈3.9 μm) and the volumetric ONH-centered protocol acquired using Cirrus HD OCT (Carl Zeiss Meditec, Dublin, CA), which covers 6×6×2 mm³ region with 200×200×1024 voxels and obtained positive results.

BMO detection was validated and the RPE segmentation was checked. Five scans from the ones used in the repeatability testing were randomly selected. An experienced grader manually selected the BMO points. This resulted in a total amount of 488 B-scans with manually selected BMO points which corresponded to the number detected automatically.

TABLE 1

Repeatability test for the 3D parameters.

| Parameters | ICC | LCI | UCI |
| --- | --- | --- | --- |
| ONH Cup Vol.($V_{cup}$) (mm³) | 0.998 | 0.996 | 0.999 |
| Central ONH Thickness (CONHT) (mm) | 0.905 | 0.813 | 0.958 |
| BMO Region Vol ($V_{bmo}$) (mm³) | 0.993 | 0.986 | 0.997 |
| ONH Total Vol. ($V_{tv}$) (mm³) | 0.995 | 0.989 | 0.998 |
| ONH Annular Vol. ($V_{av}$) (mm³) | 0.983 | 0.965 | 0.993 |
| Bending Energy ($E_b$) | 0.911 | 0.824 | 0.961 |
| BMO-MRW Surface Area ($A_{mrw}$) (mm²) | 0.910 | 0.823 | 0.960 |
| BMO-MRW ($d_{mrw}$) (mm) | 0.993 | 0.986 | 0.997 |
| BMO Area ($A_{bmo}$) (mm²) | 0.989 | 0.976 | 0.995 |

Abbreviations: ICC - intra-class correlation coefficient, LCI - lower boundary of 95% confidence interval and UCI - upper boundary of 95% confidence interval.

Furthermore, the mean signed and unsigned error in the x axis was compared, as well as in the axial one (in z axis). If the automated method identified the BMO closer to the optic disc center, the sign of distance in the x-direction was positive. Similarly, if the automated BMO located below the manual BMO, the sign of distance in the z-direction was positive. Results are shown in Table 2.

TABLE 2

| | Mean (±SD) unsigned error (pixels) | Mean (±SD) unsigned error (μm) | Mean (±SD) signed error (pixels) | Mean (±SD) signed error (μm) |
| --- | --- | --- | --- | --- |
| x axis | 4.9098 (±4.9182) | 61.8635 (±61.9693) | −0.6107 (±6.9261) | −7.6943 (±87.2693) |
| z axis | 2.8828 (±3.1801) | 12.4024 (±11.2429) | −0.3618 (±4.2790) | −1.4110 (±16.6881) |

Mean unsigned and signed error in pixel and μm, for the x axis, and z axis between automatic (proposed) and manual segmentation.

Clinical Evaluation

In this section, the results of the method according to the invention for 248 OCT scans are presented, from three groups, 71 healthy control eyes (HC), 31 eyes of patients suffering from idiopathic intracranial hypertension (IIH), which causes swelling of the ONH (papilledema). We also included 146 eyes of patients with autoimmune central nervous system disorders (multiple sclerosis (MS) and nueromyelitis spectrum disorder (NMOSD)) and a history of optic neuritis (ON), an inflammatory optic neuropathy that damages the optic nerve leading to neuroaxonal degeneration.

In IIH patients, the ONH volume is increased and was shown to correlate with cerebrospinal fluid (CSF) pressure. The longitudinal analyses revealed that ONH volume measured by OCT decreased after the initial lumbar puncture and initiation of therapy with acetazolamide. Additionally, increased ONH volume was associated with lower visual acuity in IIH patients, which points out to the potential clinical relevance of the parameter.

ON is one of the most common initial clinical presentations of MS without any prior history of a demyelinating event. During the course of the disease, acute ON affects 50%, 70% of MS patients. After initial swelling due to edema in the acute phase of ON, retinal nerve fiber layer (RNFL) thickness decreased over the following 6 months. Optic neuritis (ON) is the first NMOSD-related clinical event in 55% of the patients, which causes severe structural damage to the optic nerve and retina with resulting functional impairment. Recurrent ONs in NMOSD give rise to severely thinned pRNFL and combined ganglion cell layer and inner plexiform layer (GCIP).

The results presented in Table 3 demonstrate that the method according to the invention successfully captures the differences. The only parameter showing no difference between groups is bending energy, $E_b$. Although it was expected that in the IIH affected eyes the ONH shape inside the BMO to have a smoother convex shape, the data is still extremely heterogeneous. Thus, the bending energy reflects this extreme variability in the data.

Especially inside the BMO the topologies from one ONH to the other can be extremely different.

TABLE 3

| Parameters | HC | | IIH | | ON | | GEE | | |
|---|---|---|---|---|---|---|---|---|---|
| | Mean (SD) | Min-Max | Mean (SD) | Min-Max | Mean (SD) | Min-Max | p(HC-IIH) | p(HC-ON) | p(IIH-ON) |
| ONH Cup Vol.($V_{cup}$) ($mm^3$) | 0.044 (0.075) | 0.000-0.370 | 0.004 (0.012) | 0.000-0.049 | 0.035 (0.052) | 0.000-0.256 | 0.0012 | 0.353 | 1.95E−07 |
| Central ONH Thickness (CONHT) (mm) | 0.002 (0.25) | −0.545-0.550 | 0.403 (0.340) | −0.242-0.966 | 0.012 (0.231) | −0.399-0.668 | 9.91E−06 | 0.747 | 4.22E−06 |
| BMO Region Vol ($V_{bmo}$) ($mm^3$) | 0.572 (0.21) | 0.107-1.035 | 1.521 (1.022) | 0.436-4.3098 | 0.444 (0.189) | 0.105-1.050 | 5.02E−05 | 0.0012 | 2.66E−06 |
| ONH Total Vol. ($V_{tv}$) ($mm^3$) | 2.523 (0.250) | 2.114-2.988 | 3.309 (0.799) | 2.351-5.365 | 2.163 (0.295) | 1.522-3.087 | 2.57E−05 | 5.28E−13 | 6.54E−10 |
| ONH Annular Vol. ($V_{av}$) ($mm^3$) | 1.906 (0.181) | 1.504-2.268 | 1.78 (0.357) | 0.572-2.200 | 1.683 (0.210) | 1.162-2.118 | 0.146 | 2.19E−10 | 0.257 |
| Bending Energy ($E_b$) | 0.026 (0.009) | 0.011-0.065 | 0.029 (0.013) | 0.008-0.066 | 0.029 (0.010) | 0.011-0.066 | 0.477 | 0.038 | 0.793 |
| BMO-MRW Surface Area ($A_{mrw}$) ($mm^2$) | 1.791 (0.459) | 0.763-2.789 | 2.975 (1.016) | 1.439-5.351 | 1.414 (0.364) | 0.615-2.765 | 1.35E−06 | 5.44E−06 | 3.94E−11 |
| BMO-MRW ($d_{mrw}$) | 0.135 (0.054) | 0.261-0.035 | 0.263 (0.105) | 0.127-0.447 | 0.093 (0.040) | 0.030-0.260 | 3.52E−07 | 2.69E−05 | 1.81E−12 |
| BMO Area ($A_{bmo}$) ($mm^2$) | 1.906 (0.352) | 1.158-2.646 | 2.682 (1.109) | 1.057-5.709 | 1.861 (0.377) | 1.030-3.326 | 0.0028 | 0.407 | 0.001 |

Table 3: Analysis of all the 3D parameters defined for the HC and patient group. The last column shows the GEE analysis between the two groups. Abbreviations: HC—healthy controls. SD—standard deviation, Min—minimum value, Max—maximum value, GEE—generalized estimating equation models analysis accounting for the inter-eye/intra-subject dependencies, p—p value.

Figure 8:
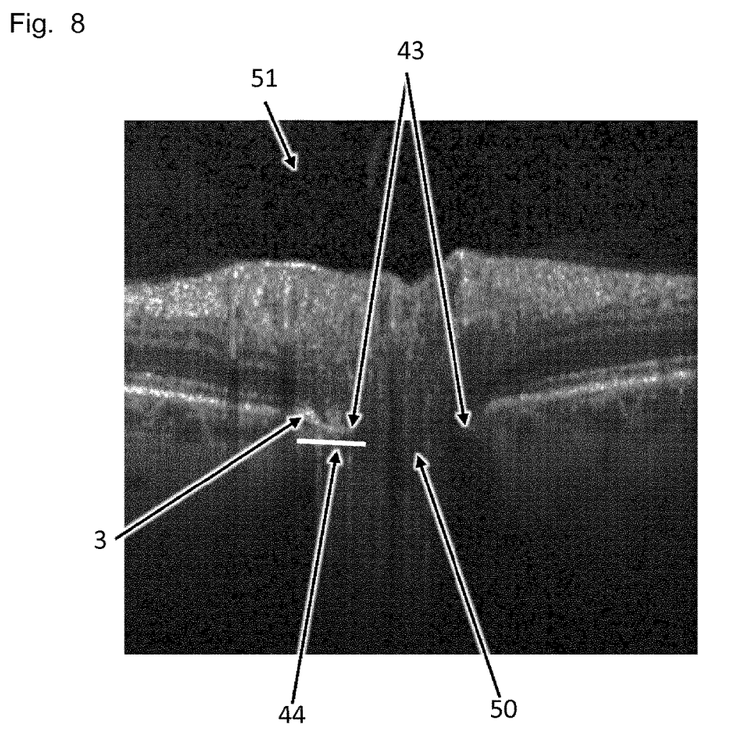
FIG. 8 a B-scan of the ONH, where the Bruch's membrane is visible close to the ONH.

In FIG. 8 it is exemplary shown in which region the Bruch's membrane can be seen in a OCT scan. Close to the optic nerve head, the RPE portion 3 ends and the Bruch's membrane 44 (underlined by a white bar) is visible as a continuation of the RPE 3. At the end points of the Bruch's membrane 44 the Bruch's membrane openings 43 are visible that can be identified as well by the method according to the invention.

Moreover, the border tissue of Elsching 50 is also visible in this OCT scan. The vitreous 51 is also indicated in this OCT-scan.

With the proposed method that can be implemented in a computer for execution, it is possible to efficiently and accurately determine several morphologic parameters, particularly a bending energy that provides a novel morphologic parameter characterizing the optic nerve head.

REFERENCES

[1] E. M. Kadas, F. Kaufhold, C. Schulz, et al., 3D Optic Nerve Head Segmentation in Idiopathic Intracranial Hypertension, 262-267. Springer Berlin Heidelberg, Berlin, Heidelberg (2012).

[2] C.-L. Chen, H. Ishikawa, G. Wollstein, et al., "Individual a-scan signal normalization between two spectral domain optical coherence tomography devices," Investigative Ophthalmology & Visual Science 54(5), 3463-3471 (2013).

[3] M. K. Garvin, M. D. Abramoff, R. Kardon, et al., "Intraretinal layer segmentation of macular optical coherence tomography images using optimal 3d graph search," IEEE Transactions on Medical Imaging 27, 1495-1505 (2008).

[4] B. J. Antony, A Combined Machine-learning and Graph-based Framework for the 3-d Automated Segmentation of Retinal Structures in Sd-oct Images. PhD thesis, Iowa City, IA, USA (2013). AAI3608177.

[5] K. Rohr, H. S. Stiehl, R. Sprengel, et al., Point-based elastic registration of medical image data using approximating thin-plate splines, 297-306. Springer Berlin Heidelberg, Berlin, Heidelberg (1996).

[6] A. S. C. Reis, N. O'Leary, H. Yang, et al., "Influence of clinically invisible, but optical coherence tomography detected, optic disc margin anatomy on neuroretinal rim evaluation," Investigative Ophthalmology & Visual Science 53(4), 1852-1860 (2012).

The invention claimed is:

1. A method for automatic shape quantification of an optic nerve head from three-dimensional image data acquired with optical coherence tomography, comprising the steps of:
   a) Providing three-dimensional image data of the retina, the image data comprising at least a portion of the optic nerve head, wherein the image data comprises pixels with associated pixel values;
   b) In the three-dimensional image data identifying anatomic portions of the optic nerve head, the anatomic portions comprising a retinal pigment epithelium, portion and an inner limiting membrane, ILM, portion;
   c) Determining an RPE polygon mesh for a lower boundary of the retinal pigment epithelium portion, wherein the RPE polygon mesh extends along the lower boundary of the retinal pigment epithelium portion;
   d) Determining an ILM polygon mesh for the inner limiting membrane portion, wherein the ILM polygon mesh extends along the inner limiting membrane portion;
   e) Determining a morphologic parameter of the optic nerve head from the RPE polygon mesh and the ILM polygon mesh;
      wherein the RPE polygon mesh and the ILM polygon mesh each comprise vertices and faces and edges, wherein for each face of the ILM polygon mesh a corresponding vertex of the RPE polygon mesh is determined, such that a correspondence between the ILM polygon mesh and RPE polygon mesh is determined; and
   f) Displaying the morphologic parameter of the optic nerve head and/or a representation of at least a portion of the RPE polygon mesh and/or a representation of at least a portion of the ILM polygon mesh.

2. Method according to claim 1, wherein in the image data openings in the Bruch's membrane, BMO, are automatically identified, wherein from the identified Bruch's membrane openings a set of points is generated representing the Bruch's membrane openings, wherein the set of points encloses a Bruch's membrane opening region.

3. Method according to claim 2, wherein an oval is fitted to the points representing the Bruch's membrane openings, wherein the oval encloses the Bruch's membrane opening region and wherein the oval is comprised by a plane-extending orthogonally to an A-scan direction of the image data.

4. Method according to claim 3, wherein the oval is transformed to a circle by an affine transformation.

5. Method according to claim 2, wherein for the RPE polygon mesh a central RPE region and for the ILM polygon mesh a central ILM region is determined, wherein the respective central region is enclosed by an area corresponding to a projection of the oval onto the respective polygon mesh, wherein the projection is along the A-scan direction of the image data.

6. Method according to claim 1, wherein an optic nerve head cup volume is determined, wherein the optic nerve head cup volume is calculated from the ILM and RPE polygon mesh, wherein the optic nerve head cup volume is the volume enclosed by the portion of the ILM polygon mesh that extends below the RPE polygon mesh.

7. Method according to claim 1, wherein an optic nerve head cup surface is calculated from the RPE polygon mesh and the ILM polygon mesh, wherein the optic nerve head cup surface corresponds to the surface portion of the ILM polygon mesh that extends below the RPE polygon mesh.

8. Method according to claim 1, wherein a bending energy is determined for the inner limiting membrane portion from the ILM polygon mesh, wherein the bending energy corresponds to a magnitude of curvature of the ILM polygon mesh, wherein the bending energy is determined only for the central ILM region.

9. Method according to claim 1, wherein the RPE polygon mesh and/or the ILM polygon mesh is a triangulated surface, wherein for each face of the ILM triangulated surface a corresponding vertex of the RPE triangulated surface is determined, such that a correspondence between the ILM triangulated surface and the RPE triangulated surface is established.

10. Method according to claim 1, wherein prior to the determination of the RPE polygon mesh for the retinal pigment epithelium portion said portion is smoothed by means of a thin plate spline method, wherein the smoothing is applied to the lower boundary of the retinal pigment epithelium or wherein the smoothing is applied only to the lower boundary of the retinal pigment epithelium, wherein the RPE polygon mesh is determined for the lower boundary of the smoothed retinal pigment epithelium portion.

11. Method according to claim 1, wherein prior to the determination of the RPE polygon mesh for the lower boundary of the retinal pigment epithelium portion said portion is interpolated by means of a thin plate spline method for the Bruch's membrane opening region, wherein the RPE polygon mesh is determined for the interpolated lower boundary of the retinal pigment epithelium portion.

12. Method according to claim 1, wherein a transformation is determined under which retinal pigment epithelium portion becomes planar, wherein the image data and/or the ILM polygon mesh, the RPE polygon mesh and the Burch membrane openings are transformed by the same transformation.

13. A computer program comprising instructions to cause a computer to execute the steps of the method of claim 1.

* * * * *